(12) United States Patent
Dubrowny et al.

(10) Patent No.: US 6,686,204 B2
(45) Date of Patent: Feb. 3, 2004

(54) COLLECTION DEVICE

(75) Inventors: Nancy E. Dubrowny, Garfield, NJ (US); Andrew J. Harrop, Okehampton (GB)

(73) Assignee: Becton, Dickinson & Company, Franklin Lakes, NJ (US)

( * ) Notice: Subject to any disclaimer, the term of this patent is extended or adjusted under 35 U.S.C. 154(b) by 0 days.

(21) Appl. No.: 10/226,714

(22) Filed: Aug. 23, 2002

(65) Prior Publication Data

US 2003/0045857 A1 Mar. 6, 2003

Related U.S. Application Data

(60) Provisional application No. 60/315,107, filed on Aug. 27, 2001.

(51) Int. Cl.[7] .............................. G01N 33/86; B01L 3/00
(52) U.S. Cl. .......................... 436/69; 422/73; 422/102; 600/369; 73/64.41; 435/13; 604/416
(58) Field of Search .......................... 422/99, 102, 73, 422/939, 940; 436/69; 600/368, 369; 73/64.41; 435/13; 604/416

(56) References Cited

U.S. PATENT DOCUMENTS

| | | | | |
|---|---|---|---|---|
| 4,257,886 A | * | 3/1981 | Kessler | 210/516 |
| 4,836,987 A | * | 6/1989 | Shibata et al. | 422/101 |
| 5,246,666 A | * | 9/1993 | Vogler et al. | 422/73 |
| 5,320,812 A | * | 6/1994 | Harper | 422/102 |
| 5,326,535 A | * | 7/1994 | Vogler et al. | 422/102 |
| 5,378,431 A | * | 1/1995 | Vogler et al. | 422/73 |
| 5,455,009 A | * | 10/1995 | Vogler et al. | 422/102 |
| 5,634,474 A | * | 6/1997 | Grippi | 600/576 |
| 6,534,016 B1 | * | 3/2003 | Cohen et al. | 422/102 |

FOREIGN PATENT DOCUMENTS

| | | | |
|---|---|---|---|
| EP | 0 073 551 | | 3/1983 |
| EP | 0 628 816 | | 12/1994 |
| JP | 11-318866 | * | 11/1994 |
| JP | 2000-228 | * | 1/2000 |
| JP | 2000-229 | * | 1/2000 |
| WO | 00/06225 | * | 2/2000 |

* cited by examiner

Primary Examiner—Maureen M. Wallenhorst
(74) Attorney, Agent, or Firm—Hoffman & Baron, LLP

(57) ABSTRACT

The present invention is a container assembly that includes a coating composition on an interior surface of the container assembly and more particularly a coating composition for rapid clotting of a blood sample within a blood collection tube. The coating composition includes an intrinsic coagulation activator and an extrinsic coagulation activator for activating intrinsic and extrinsic pathways for promoting the rapid clotting of the blood sample. In addition, the present invention includes a barrier package for enclosing the container assembly.

31 Claims, 5 Drawing Sheets

COLLECTION DEVICE

CROSS-REFERENCE TO RELATED APPLICATIONS

This application claims priority to U.S. Provisional Application No. 60/315,107, filed Aug. 27, 2001, the contents of which are incorporated herein by reference.

BACKGROUND OF THE INVENTION

1. Field of the Invention

The present invention relates to a multi-layer coating composition in a container for promoting rapid clotting of a blood sample, methods for applying the multi-layer coating composition in a container such as a blood collection device and a barrier package for the blood collection device.

2. Description of Related Art

Blood samples are routinely taken in evacuated collection tubes. One end of a double-ended needle is inserted into a patient's vein. The other end of the needle then punctures a septum covering the open end of the tube so that the vacuum in the tube draws the blood sample through the needle into the tube. Using this technique, a plurality of samples can be taken using a single needle puncture of the skin.

Blood collected in evacuated tubes often must be clotted prior to clinical examination. It is desirable to form a dense clot as rapidly and completely as possible to facilitate clean separation of the clot from the serum layer by centrifugation. To achieve this, collection tubes frequently employ a clot activator. Typical activators are diatomaceous earth and particles of inorganic silicates, or biochemicals such as ellagic acid, thrombin and thromboplastin.

Two types of activators, classified in the art according to the portion of the blood coagulation cascade stimulated, are conventionally employed. Particulate activators share a common biochemical mechanism of clot activation known as contact activation of the intrinsic pathway. Whole blood contains all of the necessary factors to cause clotting by the intrinsic pathway. Clot activation by the intrinsic pathway is surface area dependent, i.e., the time required to form a complete blood clot is dependent on the total number of activating surface sites per unit area on the activator surface relative to the volume of blood. Greater surface area, provided by finely divided particulate activators, leads to shorter clot times. Particulate activators are used in practically all commercial blood collection tubes and lead to dense, crosslinked clots that cleanly separate from the serum in a centrifuge. Clot formation, however, is relatively slow, and about 30–60 minutes are required prior to centrifugation. Typical particulate activators used commercially are silica impregnated in fabric silica particles in small plastic cups or silicate particles applied to the tube wall in polyvinylpyrrolidone (PVP).

The second type of clot activators induces clotting through a different part of the coagulation cascade known in the art as the extrinsic pathway. The extrinsic system relies on the presence of a substance not normally present in whole blood. Activation is biochemical in nature and is concentration dependent. Clot activation rates lead to clot formation in 10–20 minutes, but clots resulting from the extrinsic pathway are gelatinous in nature and do not cleanly separate from serum.

There is a need for a blood collection tube with means for promoting clot acceleration of a blood sample which provides an enhanced rate of blood coagulation but which does not remain in the serum layer but becomes part of the clot upon centrifugation, thus avoiding potential interference with clinical tests.

SUMMARY OF THE INVENTION

The present invention is a container with means for promoting clot acceleration of a blood sample. Desirably, the container comprises a coating of an intrinsic coagulation activator and an extrinsic coagulation activator.

Preferably, the intrinsic coagulation activator is diatomaceous earth or ground silica. Most preferably, the intrinsic coagulation activator is ground silica. Desirably, the intrinsic activator, for example ground silica, is applied with polyvinylpyrrolidone.

Desirably, the extrinsic coagulation activator is ellagic acid or a protein. Preferably, the extrinsic coagulation activator is thrombin, heparinase or fibrinogen. Most preferably, the extrinsic coagulation activator is thrombin.

The intrinsic coagulation activator and the extrinsic coagulation activator are applied to interior surfaces of a container, such as a blood collection tube, in the form of mixtures or solutions. The mixtures or solutions are dried to form layers of the activators. Additionally, other layers of additional materials may suitably be applied. Alternatively, different activators and materials may be mixed to form combined solutions which may be applied and dried to form a layer or layers having the combined attributes of the solution constituents.

In one aspect of the present invention, the means for promoting clot acceleration is applied as a dual-layered coating to the inside of a container as follows:

(a) mixing polyvinylpyrrolidone (PVP) and an intrinsic coagulation activator in water to form a first mixture;

(b) spraying the first mixture onto the inner surface of the container;

(c) drying the first mixture to form a first coating layer;

(d) mixing an extrinsic coagulation activator with water to form a second mixture;

(e) spraying the second mixture onto the first coating layer; and (f) drying the second mixture to form a second coating layer.

Preferably, the means for promoting clot acceleration is applied as a dual-layered coating to the inside of a container as follows:

(a) mixing polyvinylpyrrolidone (PVP), an intrinsic coagulation activator and a water soluble surfactant in water to form a first mixture;

(b) spraying the first mixture onto the inner surface of the container;

(c) drying the first mixture to form a first coating layer;

(d) mixing an extrinsic coagulation activator with water to form a second mixture;

(e) spraying the second mixture onto the first coating layer; and (f) drying the second mixture to form a second coating layer.

More preferably, the means for promoting clot acceleration is applied as a dual-layered coating to the inside of a container as follows:

(a) mixing polyvinylpyrrolidone (PVP), ground silica and a water soluble silicone surfactant in water to form a first mixture;

(b) spraying the first mixture onto the inner surface of the container;

(c) drying the first mixture to form a first coating layer;
(d) mixing thrombin with water to form a second mixture;
(e) spraying the second mixture onto the first coating layer; and
(f) drying the second mixture to form a second coating layer.

In another aspect of the present invention, the means for promoting clot acceleration is applied as a three-layered coating to the inside of a container as follows:
 (a) mixing a water soluble surfactant with water to form a first mixture;
 (b) spraying the first mixture onto the inner surface of the container;
 (c) drying the first mixture to form a first coating layer;
 (d) mixing polyvinylpyrrolidone (PVP) and an intrinsic coagulation activator in water to form a second mixture;
 (e) spraying the second mixture onto the first coating layer;
 (f) drying the second mixture to form a second coating layer;
 (g) mixing an extrinsic coagulation activator with water to form a third mixture;
 (h) spraying the third mixture onto the second mixture; and
 (i) drying the third mixture to form a third coating layer.

Desirably, the means for promoting clot acceleration is applied as a three-layered coating to the inside of a container as follows:
 (a) mixing a water soluble silicone surfactant with water to form a first mixture;
 (b) spraying the first mixture onto the inner surface of the container;
 (c) drying the first mixture to form a first coating layer;
 (d) mixing polyvinylpyrrolidone (PVP) and ground silica in water to form a second mixture;
 (e) spraying the second mixture onto the first mixture;
 (f) drying the second mixture to form a second coating layer;
 (g) mixing thrombin with water to form a third mixture;
 (h) spraying the third mixture onto the second mixture; and
 (i) drying the third mixture to form a third coating layer.

In addition, the container with the intrinsic and extrinsic coagulation activators is provided in a moisture impermeable receptacle with a moisture absorbing material. The moisture impermeable receptacle with a moisture absorbing material maintains the integrity of the thrombin in the container. Since thrombin may degrade when exposed to high external humidity, the integrity for promoting clot acceleration of a blood sample with thrombin is found to be maintained in a moisture impermeable receptacle.

Most notably, the present invention provides the means for promoting clot acceleration of a blood sample at a faster rate than when only silica is used.

In addition, the present invention provides the means for promoting clot acceleration of a blood sample even when exposed to high humidity.

DETAILED DESCRIPTION

The present invention may be embodied in other specific forms and is not limited to any specific embodiment described in detail which is merely exemplary. Various other modifications will be apparent to and readily made by those skilled in the art without departing from the scope and spirit of the invention. The scope of the invention will be measured by the appended claims and their equivalents.

Figure 1:
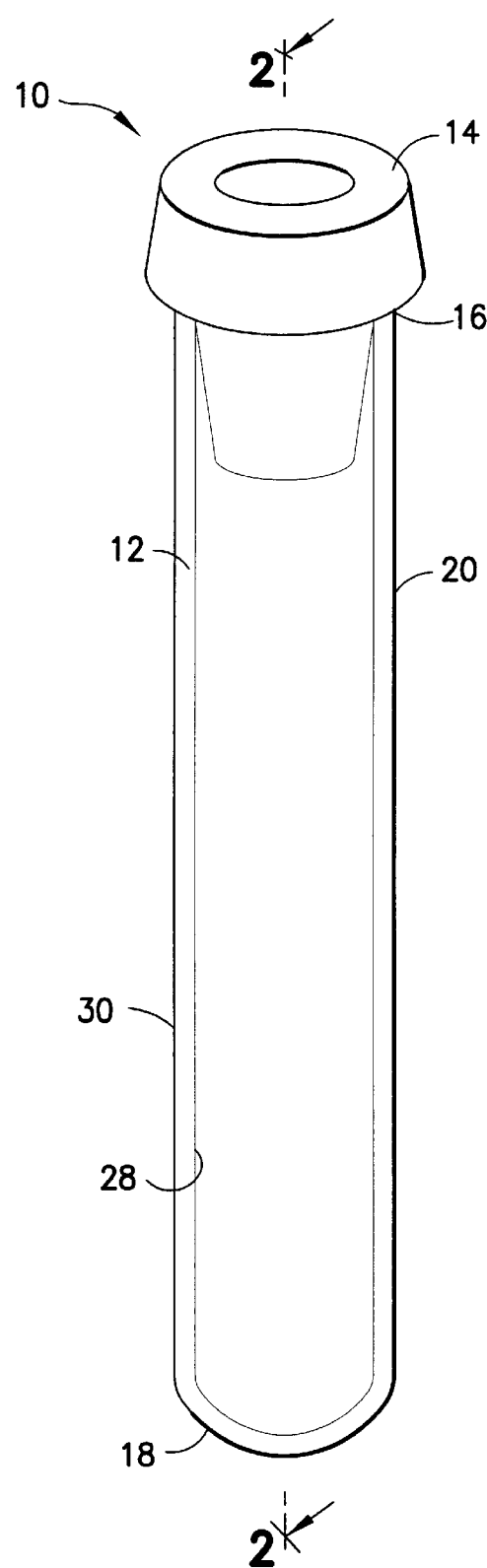
FIG. 1 is a perspective view of a collection assembly of the present invention.

Referring to the drawings in which like reference characters refer to like parts throughout the several views thereof in FIG. 1, shows a collection assembly 10 comprising a generally cylindrical tube 20 and a closure 14. The tube 20 includes a sidewall 12 extending from an open end 16 to a bottom closed end 18. Sidewall 12 further includes an inner wall surface 28 and an outer wall surface 30 to define a wall thickness therebetween. Any useful wall thickness may suitably be used, but a non-limiting wall thickness of about 25 mil (or about 0.6 mm) to about 50 mil (or about 1.2 mm) is desirable. Closure 14 may be an elastomeric stopper, as is well known in the art of evacuated blood collection tubes. Desirably, closure 14 is a puncturable closure.

Figure 2:
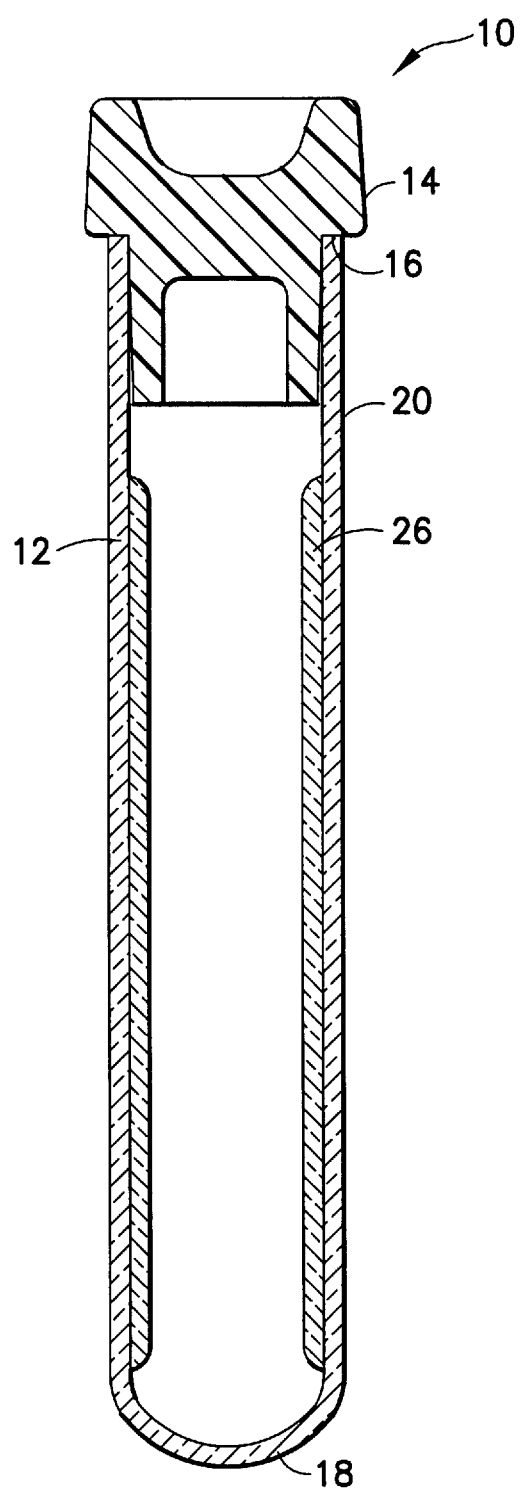
FIG. 2 is a cross-sectional view of the assembly of FIG. 1 depicting portions of the inner surface of the assembly having a coating of the present invention for promoting clot acceleration.

As shown in FIG. 2, the coating 26 of the present invention for promoting clot acceleration is located on inner wall surface 28 of the assembly 10. The coating 26 comprises an intrinsic coagulation activator and an extrinsic activator. The coating 26 may further include a surfactant.

Preferably, the intrinsic coagulation activator is diatomaceous earth or ground silica. Most preferably, the intrinsic coagulation activator is ground silica. Useful, but non-limiting, ground silicas include ground silicas having small particle sizes, for example an average particle size of about 15 microns or less. Desirably, the ground silica has an average particle size of about 10 microns or less, for example an average particle size from about 1 to about 5 microns. Such ground silicas are commercially available, for example from U.S. Silica Company, WV.

Desirably, the intrinsic coagulation activator, for example ground silica, is applied with polyvinylpyrrolidone. Desirably, the polyvinylpyrrolidone has a molecular weight from about 20,000 daltons to about 1,500,000 daltons. More desirably, the polyvinylpyrrolidone has a molecular weight from about 30,000 daltons to about 70,000 daltons. A polyvinylpyrrolidone with a molecular weight of about 58,000 daltons is also useful. Such polyvinylpyrrolidones are commercially available, for example from International Specialty Products, Surrey, UK.

Desirably, the extrinsic coagulation activator is ellagic acid or a protein. Preferably, the extrinsic coagulation activator is thrombin, heparinase or fibrinogen. Most preferably, the extrinsic coagulation activator is thrombin. Desirably, the thrombin is bovine thrombin having at least 50% protein and having greater than 75 NIH units/mg protein. Such thrombin is commercially available from Scientific Protein Laboratories, Inc, WI.

Desirably, the surfactant is a water soluble surfactant. Preferably, the water soluble surfactant is a water soluble silicone surfactant. Useful, but non-limiting, water soluble silicone surfactants include commercially available polyalkyleneoxide modified polydimethylsiloxane surfactants from Crompton Corporation, SC.

Figure 2A:
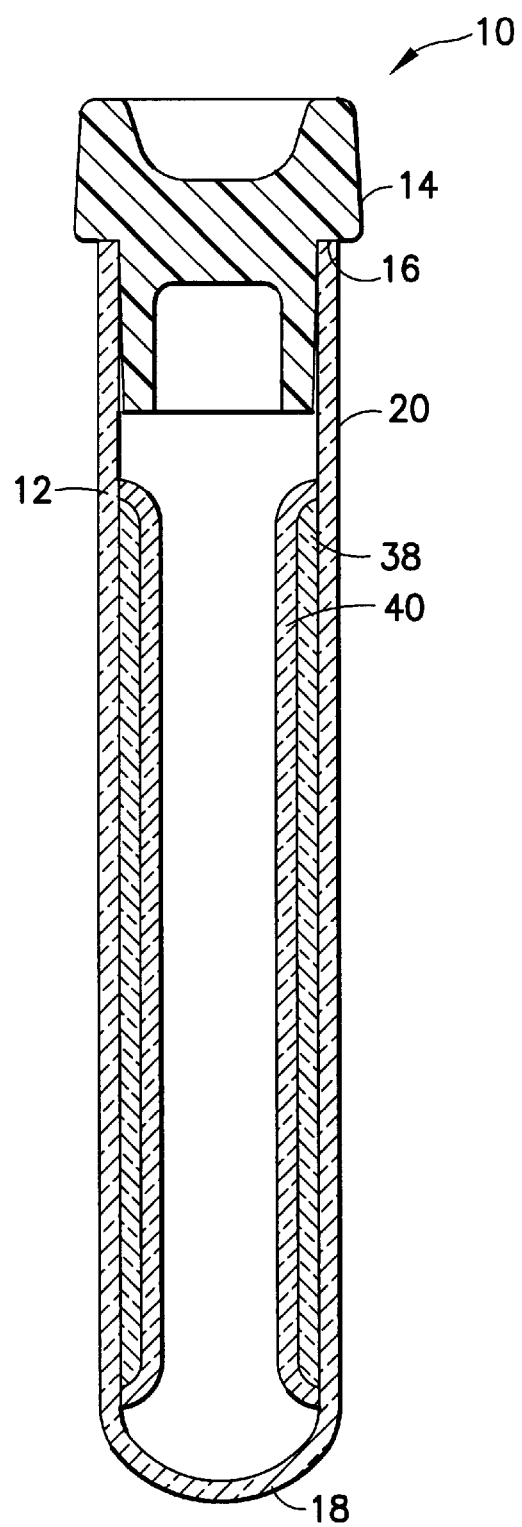
FIGS. 2A and 2B are cross-sectional views of the assembly of FIG. 1 depicting portions of the inner surface of the assembly having multi-layer coatings of the present invention for promoting clot acceleration.

As depicted in FIG. 2A, the coating 26 is a multi-layer coating comprising a first layer 38 of a mixture of a surfactant and an intrinsic coagulation activator and a second layer 40 of an extrinsic activator. Desirably, the first layer 38 comprises a water soluble silicone surfactant and ground silica and second layer 40 comprises thrombin.

Figure 2B:
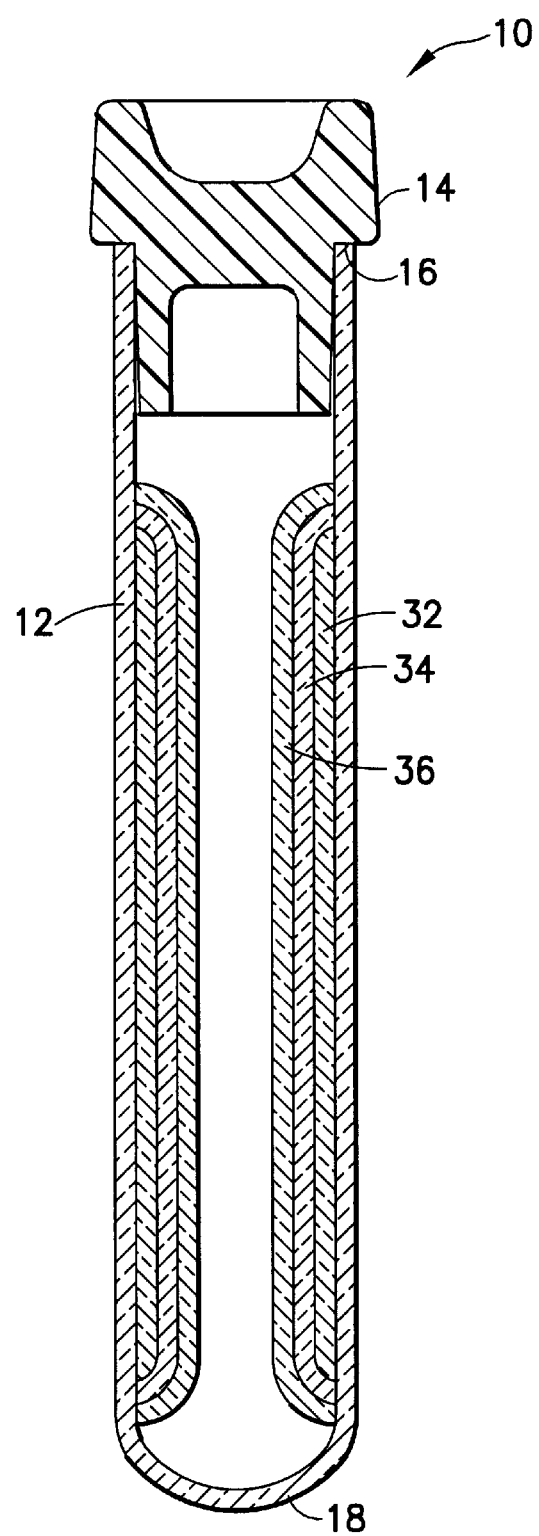

As depicted in FIG. 2B, the coating 26 is a multi-layer coating comprising a first layer 32 of a surfactant, a second layer 34 of an intrinsic coagulation activator and a third layer 36 of an extrinsic coagulation activator. Desirably, the first layer 32 comprises a water soluble silicone surfactant, the second layer 34 comprises ground silica and third layer 36 comprises thrombin.

The tube 20 of collection assembly 10 is preferably a plastic tube, but may be a glass tube. Suitable plastic materials include polyvinyl chloride, polypropylene (PP), polystyrene (PS) and polyethylene terephthalate (PET). Desirably, the tube 20 of the collection assembly 10 is a polyethylene terephthalate plastic. The tube 20 of the collection assembly 10 may be made by extrusion processes or injection molding processes followed bottom sealing steps, such as induction heating, ultrasonic, hot plate, spin or solvent welding or adhesive bonding. Alternatively, the tube 20 of the collection assembly 10 may also be made completely in a molding cavity by injection molding.

While the tube 20 of the collection assembly 10 may be of any size, the invention is particularly suited to evacuated blood collection tubes. Useful evacuated blood collection tubes typically have, but are not limited to, a length from about 50 mm to about 150 mm and a diameter from about 10 mm to about 20 mm. Desirably, the tube 20 is a PET tube having a diameter of about 13 mm and a length of about 75 mm or about 100 mm. Such tubes are useful for obtaining from about 2 to 6 ml of blood. Alternatively, the tube 10 may be a microcollection tube having smaller dimension than the evacuated blood collection tubes for obtaining smaller samples of blood.

Figure 3:
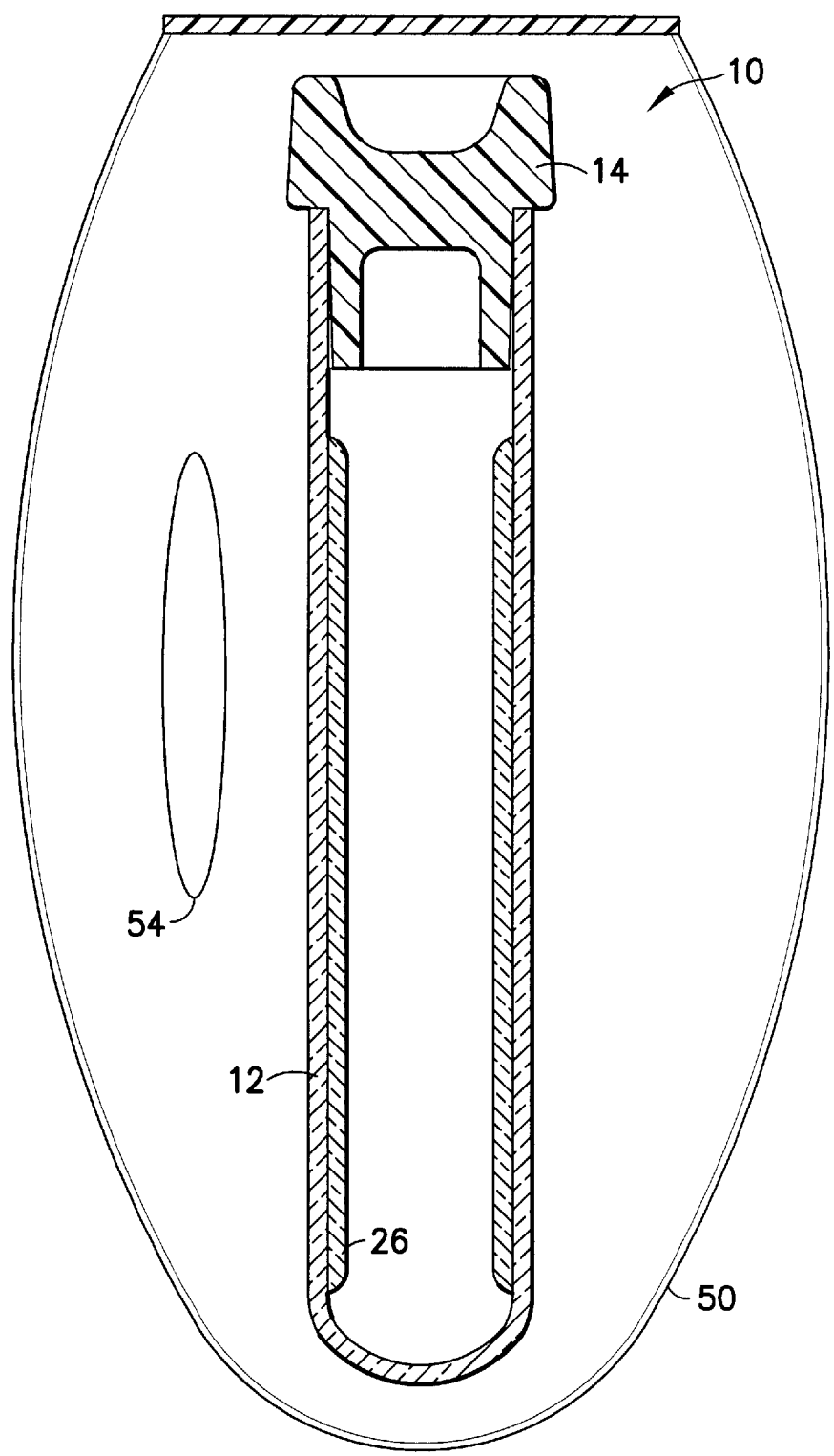
FIG. 3 is a perspective view of the assembly of FIG. 2 in a pouch assembly.

FIG. 3 shows the collection assembly in a pouch 50. Within pouch 50 is a moisture absorbing material 54. If the collection assembly is substantially impermeable to moisture transmission, then a pouch assembly is not necessary. However, when moisture penetration is a concern, the collection assembly may be placed within pouch 50. As used herein, the phrase "substantially impermeable to moisture transmission" and it variants refer to a water vapor transmission rate per unit surface of material of less than or equal to about 1.0 g/m$^2$/day.

It was found during testing of the present plastic collection assembly that when thrombin was used as an extrinsic activator, high levels of humidity caused degradation of the thrombin. Moisture penetrating the plastic receptacle walls was determined to be the causative agent. Thus, the present plastic collection device is most preferably packaged within an impermeable pouch containing a moisture absorbing material.

Pouch 50 is preferably of an aluminum foil laminated with LDPE/OPET/adhesive/sealant. LDPE/OPET is a low density polyethylene/oriented polyethylene terephthalate. Desirably, such a laminate is substantially impermeable or impermeable to moisture transmission, i.e., having a water vapor transmission rate of less than or equal to about 1.0 g/m$^2$/day. More desirably, the water vapor transmission rate of the laminate is less than or equal to about 0.2 g/m$^2$/day. The layering also provides mechanical protection of the foil, heat sealing and opening features. Additionally, pouch 50 is preferably packaged with moisture absorbing material 54 (desiccant) which may be of silica dioxide (silica gel) or moisture absorbing beads, rods, sheets, or sachets and which may incorporate warning colors and/or wording which appear when the moisture content exceeds a certain level. Pouch 50 may accommodate one or more collection assemblies.

The tube 20 of the collection assembly 10 of the present invention may suitably be coated with a multi-layer coating of intrinsic coagulation activator and extrinsic coagulation activator as described below. The method described is for tube 10 suitable for a nominal 6 ml draw sample of blood. Such a tube is nominally 13 mm in diameter and 100 mm in length. Additionally, details are shown for a tube 10 having a nominal 4.8 ml draw sample of blood, which is nominally 13 mm in diameter and 75 mm in length. Such tube dimensions are of course non-limiting.

In one aspect of the present invention, a thrombin coating solution is prepared to have about 2,500 NIH units/ml concentration of thrombin. Thrombin is commercially available in the form of a powder and the thrombin powder activity in NIH units is determined. The required quantity of thrombin powder required to be dissolved in water to achieve about 2,500 NIH units/ml is calculated from the thrombin powder activity. The required quantity of thrombin powder is combined in about 50% of total water volume and mixed until dissolved. The remaining water is added to obtain the final volume and concentration of the thrombin coating solution. The thrombin coating solution may be stored at a refrigerated temperature, for example less than about 8° C., for a suitable period of time, for example about 5 days or less.

A silica coating solution is also prepared. First, the total or final volume of water required for production run is determined. About 60% of this volume of water is added to a mixing vessel, but other quantities may suitably be added. About 7 g/l of final volume of polyvinylpyrrolidone (PVP) is added to the mixing vessel. About 9 g/l of final volume of silicone is added to the mixing vessel. About 35 g/l of final volume of a ground silica is added to the mixing vessel. This combination is mixed for a further 5 minutes then the remaining water is added. Mixing for a further 15 minutes is desirably. The solution is assayed to determine the concentration of silica. The solution may be stored at room temperature and used within a useful period of time, for example within about 20 hours.

Plastic tubes (PET) are placed in processing trays with their open end up. The tubes, for example the 6.0 ml draw or the 4.8 ml draw tubes, are internally coated with an amount for example about 0.32 mg, of silica through use of a silica coating machine. A tray of tubes are placed into a silica coating machine and having its reservoir filled with the silica solution. The silica coating machine uses spray heads and automatic equipment to internally coat tubes with 12 micro liters of the silica solution. The tubes are then removed from the coating machine and the tubes then pass under drying station, which is maintained at about 75° C. to about 100° C., for 30 seconds to remove the water fraction and thereby forming a first coating layer.

Desirably, the plastic tubes of the present invention are internally coated with from about 0.1 mg of silica to about 0.4 mg of silica. More desirably, the tubes are coated from about 0.3 mg of silica to about 0.4 mg of silica. Preferably, the tubes are coated with about 0.32 mg of silica.

Desirably, the plastic tubes of the present invention are internally coated with silica per internal surface area from about 0.01 $\mu$g/mm$^2$ to about 1.0 $\mu$g/mm$^2$. More desirably, the tubes are coated from about 0.05 $\mu$g/mm$^2$ to about 0.5 $\mu$g/mm$^2$ of silica per internal surface area. Preferably, the tubes are coated from about 0.05 $\mu$g/mm$^2$ to about 0.15 $\mu$g/mm$^2$ of silica per internal surface area.

The tubes, for example the 6.0 ml draw tubes, are then internally coated with about 15 NIH units of thrombin solution. The tray of previously silica coated tubes is placed into a thrombin coating machine. The thrombin coating machine contains ultrasonic spray heads spray for applying about 6 micro liters of thrombin solution into each tube. The water fraction to evaporate at ambient temperature, but other temperatures may suitably be used. The 4.8 ml draw tubes are coated with about 12.5 NIH units per tube dispensed as 5 micro liters of solution.

Desirably, the plastic tubes of the present invention are internally coated with from about 5 NIH units of thrombin to about 30 NIH units of thrombin. More desirably, the tubes are coated from about 10 NIH units of thrombin to about 20 NIH units of thrombin. Preferably, the tubes are coated from about 10 NIH units of thrombin to about 15 NIH.

Desirably, the plastic tubes of the present invention are internally coated with thrombin per internal surface area from about 0.01 NIH units/cm$^2$ to about 2.0 NIH units/cm$^2$. More desirably, the tubes are coated from about 0.1 NIH units/cm$^2$ to about 1.5 NIH units/cm$^2$ of thrombin per internal surface area. Preferably, the tubes are coated from about 0.35 NIH units/cm$^2$ to about 0.45 NIH units/cm$^2$ of thrombin per internal surface area.

The tubes are then evacuated and closed with caps or closures. The closures are loosely placed on the open end of coated tubes. Trays having the tubes are placed inside an evacuation chamber and evacuate to required vacuum or reduced pressure. The tubes are sealed with their closures to maintain the reduced pressure. For typical tube sizes used for such thrombin-containing tubes, the range of reduced pressure normally is from about 100 mmHg (absolute) and about 160 mmHg (absolute) to achieve the desired blood draw volume at an atmospheric pressure of 760 mmHg. Subsequently, the tubes may be placed within a pouch manufactured from a vapor impervious material, such as the above-described aluminum foil laminate. A moisture absorbing material may also be placed with in the pouch. The pouch is then sealed. Moreover, the tubes may be sterilized with gamma irradiation.

In another aspect of the present invention, the silicone and silica are applied as separate coating layers. The silicone layer is applied to the interior portions of a tube by spraying a silicone solution, for example 17 $\mu$l of a 0.7 silicone solution, and drying at ambient temperature or the above-described elevated temperatures. Subsequently, an amount of silica, for example 0.32 mg of ground silica, is applied to the interior portions of the tube by spraying a silica/PVP solution, for example, 5 $\mu$l of 7% silica/9% PVP combined solution, and drying as described above.

The invention may be further understood with reference to the following non-limiting examples.

EXAMPLE 1

This example demonstrates the improved clotting activity when the present invention is utilized.

Fifteen (15) plastic (PET) tubes coated with a soluble silicone surfactant, PVP and ground silica and thrombin were used in this example as compared to glass control tubes that are untreated to show the comparative clotting efficacy of the present invention versus glass tubes.

The fifteen plastic tubes were interiorly coated with a spray of 17 $\mu$l of a 0.7% silicone solution. These coatings were dried and then a spray of 5 $\mu$l of 7% silica/9% PVP combined solution was applied to each tube. These second coatings were dried and then a spray of 6 $\mu$l of thrombin solution having about 2,500 NIH units/ml concentration of thrombin was applied to each tube. These third coating were dried.

Blood was then drawn into the tubes and the glass control tube and the plastic tubes of the present invention were mixed using 10 complete inversions and allowed to clot upright in a rack at room temperature. A stopwatch was started as soon as mixing was completed, which was used to document the individual clotting time for each tube. Each tube was checked for clotting every 30 seconds by picking the tube up out of the rack and tilting slightly to assess the status of the blood sample. A blood sample is considered clotted when there is no more liquid movement of the blood sample noted. At this point for each tube evaluated, the stopwatch was stopped and the time noted in seconds was considered as the clotting time of that individual sample. Acceptable clotting time in seconds for the glass control tube is less than 300 seconds (5 minutes). The results of this Example are reported in Table 1.

TABLE 1

| Donor | Clotting Time in Seconds: | |
|---|---|---|
| | Glass | Plastic |
| 1 | 307 | 76 |
| 2 | 161 | 115 |
| 3 | 156 | 68 |
| 4 | 286 | 76 |
| 5 | 319 | 86 |
| 6 | 259 | 118 |
| 7 | 317 | 71 |
| 8 | 198 | 118 |
| 9 | 146 | 57 |
| 10 | 183 | 140 |
| 11 | 212 | 119 |
| 12 | 161 | 118 |
| 13 | 300 | 198 |
| 14 | 190 | 157 |
| 15 | 152 | 86 |

What is claimed is:

1. A method of promoting clotting of a blood sample in a blood collection receptacle by activating intrinsic and extrinsic blood clotting pathways of the sample comprising the steps of:
   applying a coating of an intrinsic coagulation activator to an interior surface of said receptacle or to a base coating disposed on the interior surface of said receptacle; and
   applying a coating of an extrinsic coagulation activator over said coating of said intrinsic coagulation activator.

2. The method of claim 1, wherein said extrinsic coagulation activator is selected from the group consisting of thrombin, heparinase and fibrinogen.

3. The method of claim 2, wherein said extrinsic coagulation activator is thrombin.

4. The method of claim 1, wherein said intrinsic coagulation activator is ground silica.

5. The method of claim 1, wherein said step of applying said intrinsic coagulation activator further includes:
   drying said intrinsic coagulation activator to form said coating of said intrinsic coagulation activator; and
   wherein said step of applying said extrinsic coagulation activator further includes:
   drying said extrinsic coagulation activator to form said coating of said extrinsic coagulation activator.

6. The method of claim 1, wherein said applying step of said intrinsic coagulation activator further includes applying polyvinylpyrrolidone and a water soluble silicone surfactant with said intrinsic coagulation activator or applying polyvinylpyrrolidone with said intrinsic coagulation activator.

7. The method of claim 1, wherein said applying said intrinsic coagulation activator step further includes applying about 0.1 mg to about 0.4 mg of said intrinsic coagulation activator.

8. The method of claim 1, wherein said applying said extrinsic coagulation activator step further includes applying about 5 NIH units to about 30 NIH units of said extrinsic coagulation activator.

9. The method of claim 1, wherein said receptacle is a plastic blood collection receptacle.

10. The method of claim 1, further including the step of applying a water soluble silicone surfactant to the interior surface of said receptacle to provide said base coating.

11. A method of promoting clotting of a blood sample in a blood collection receptacle by activating intrinsic and extrinsic blood clotting pathways of the sample comprising the steps of:
   applying polyvinylpyrrolidone and a water soluble silicone surfactant to an interior surface of said receptacle;
   drying said polyvinylpyrrolidone and said water soluble silicone surfactant to form a first coating layer;
   applying an intrinsic coagulation activator over said first coating layer;
   drying said intrinsic coagulation activator to form a second coating layer;
   applying an extrinsic coagulation activator over said second coating layer; and
   drying said extrinsic coagulation activator to form a third coating layer.

12. The method of claim 11, wherein said extrinsic coagulation activator is selected from the group consisting of thrombin, heparinase and fibrinogen.

13. The method of claim 11, wherein said intrinsic coagulation activator is ground silica.

14. The method of claim 11, wherein said applying said intrinsic coagulation activator step further includes applying about 0.1 mg to about 0.4 mg of said intrinsic coagulation activator.

15. The method of claim 11, wherein said applying said extrinsic coagulation activator step further includes applying about 5 NIH units to about 30 NIH units of said extrinsic coagulation activator.

16. The method of claim 11, wherein said receptacle is a plastic blood collection receptacle.

17. An assembly comprising:
   a receptacle having a water vapor permeability of less than about 1.0 g/m$^2$/day; and
   an evacuated blood collection tube contained within said receptacle, said tube having a coating on an interior surface for promoting clotting of a blood sample by activating intrinsic and extrinsic pathways of the sample, said coating comprising an intrinsic coagulation activator in conjunction with an extrinsic coagulation activator.

18. The assembly of claim 17, wherein said extrinsic coagulation activator is selected from the group consisting of thrombin, heparinase and fibrinogen.

19. The assembly of claim 17, wherein said intrinsic coagulation activator is ground silica.

20. The assembly of claim 17, wherein said intrinsic coagulation activator has a concentration per unit surface area on said interior surface of said tube from about 0.01 $\mu$g/mm$^2$ to about 1.0 $\mu$g/mm$^2$.

21. The assembly of claim 17, wherein said interior surface of said tube contains from about 0.1 mg to about 0.4 mg of said intrinsic coagulation activator.

22. The assembly of claim 17, wherein said extrinsic coagulation activator has a concentration per unit surface area on said interior surface of said tube from 0.01 NIH units/cm$^2$ to about 2.0 NIH units/cm$^2$.

23. The assembly of claim 17, wherein said interior surface of said tube contains from about 5 NIH units to about 30 NIH units of said extrinsic coagulation activator.

24. The assembly of claim 17, wherein said coating includes a first coating layer of said intrinsic coagulation activator and a second coating layer of said extrinsic coagulation activator over said first coating layer.

25. The assembly of claim 17, further comprising a moisture absorbing material contained within said receptacle.

26. A blood collection tube having an interior surface with a coating, said coating comprising:
   a first coating layer comprising an intrinsic coagulation activator applied to said interior surface or applied to a base coating disposed over said interior surface; and
   a second coating layer comprising an extrinsic coagulation activator applied to said first coating layer.

27. The blood collection tube of claim 26, wherein said intrinsic coagulation activator is ground silica.

28. The blood collection tube of claim 26, wherein said first coating layer further includes polyvinylpyrrolidone and a water soluble silicone surfactant.

29. The blood collection tube of claim 26, wherein said base coating comprises a water soluble silicone surfactant.

30. The blood collection tube of claim 26, wherein said extrinsic coagulation activator is thrombin.

31. The blood collection tube of claim 26, wherein the blood collection tube is a plastic blood collection tube.

* * * * *